(12) United States Patent
Lacorte et al.

(10) Patent No.: US 10,597,608 B2
(45) Date of Patent: Mar. 24, 2020

(54) CETYLATED FATTY ACIDS, SYSTEM FOR THE PREPARATION THEREOF AND USE THEREOF

(71) Applicant: Pharmanutra S.P.A., Pisa (IT)

(72) Inventors: Andrea Lacorte, Pisa (IT); Germano Tarantino, Pisa (IT); Paolo Bondioli, Milan (IT)

(73) Assignee: PHARMANUTRA S.P.A., Pisa (IT)

( * ) Notice: Subject to any disclaimer, the term of this patent is extended or adjusted under 35 U.S.C. 154(b) by 0 days.

(21) Appl. No.: 15/750,485

(22) PCT Filed: Aug. 9, 2016

(86) PCT No.: PCT/IB2016/054788
§ 371 (c)(1),
(2) Date: Feb. 5, 2018

(87) PCT Pub. No.: WO2017/029580
PCT Pub. Date: Feb. 23, 2017

(65) Prior Publication Data
US 2019/0016991 A1    Jan. 17, 2019

(30) Foreign Application Priority Data

Aug. 14, 2015 (IT) .......................... 102015000044822

(51) Int. Cl.
*C11C 3/00* (2006.01)
*C07C 67/08* (2006.01)
(Continued)

(52) U.S. Cl.
CPC .............. *C11C 3/003* (2013.01); *A61K 31/23* (2013.01); *C07C 67/08* (2013.01); *C07C 69/24* (2013.01);
(Continued)

(58) Field of Classification Search
CPC .......... C11C 3/003; C07C 51/00; C07C 67/08; C07C 69/24
See application file for complete search history.

(56) References Cited

U.S. PATENT DOCUMENTS

| 4,113,881 A | 9/1978 | Diehl | |
| 4,874,699 A * | 10/1989 | Maruzeni | C11C 3/08 435/135 |

(Continued)

OTHER PUBLICATIONS

Bartoli et al., "Highly Efficient Solvent-Free Condensation of Carboxylic Acids with Alcohols Catalysed by Zinc Perchlorate Hexahydrate, Zn(ClO4)2•6 H2O", Adv. Synth. Catal., 2005, 347: 33-38.

(Continued)

*Primary Examiner* — Yate' K Cutliff
(74) *Attorney, Agent, or Firm* — James S. Keddie; Boziocevic, Field & Francis LLP

(57) ABSTRACT

The present invention relates to a process for preparing a mixture of cetylated fatty acids and a system for carrying out said process. Furthermore, the present invention relates to a composition comprising, or alternatively, consisting of said mixture of cetylated fatty acids. Finally, the present invention relates to said composition for use in the treatment and/or prevention of: (i) rheumatoid arthritis of inflammatory and non-inflammatory origin, in particular osteoarthritis; (ii) other inflammatory joint conditions; (iii) psoriasis, lupus, periodontal diseases or cardiovascular or heart diseases; (iv) all post-traumatic osteoarticular pathologies including sports injuries; (v) all degenerative joint pathologies (arthrosis, gonarthrosis, coxarthrosis, etc.), and (vi) inflammatory-traumatic tendon and muscular conditions. Furthermore, it is envisaged that the composition of the present invention be used in the treatment and/or prevention of the above-mentioned pathologies and disorders (i)-(vi) in association with a rehabilitative therapy. The composition (Continued)

comprising said mixture is formulated in a pharmaceutical form for oral use (novel food, supplement or medical device), i.e. in the form of a pill, pastille, capsule, tablet, granules, dispersible powder, syrup, solution or sprayable solution; for topical use, i.e. in the form of a cream, unguent, ointment, gel or spray to be used as such for application on the skin, or else for trans dermal use in the form of a patch.

9 Claims, 5 Drawing Sheets

(51) Int. Cl.
    *A61K 31/23*     (2006.01)
    *C07C 69/24*     (2006.01)
    *A61P 37/02*     (2006.01)
    *A61P 9/00*     (2006.01)
    *A61P 19/02*     (2006.01)

(52) U.S. Cl.
    CPC ............ *A61P 9/00* (2018.01); *A61P 19/02* (2018.01); *A61P 37/02* (2018.01); *Y02P 20/582* (2015.11)

(56) References Cited

U.S. PATENT DOCUMENTS

| | | | |
|---|---|---|---|
| 5,898,077 A * | 4/1999 | Takahara | C07C 67/58 554/167 |
| 8,815,282 B1 * | 8/2014 | Leonard | C07C 67/08 424/451 |
| 2005/0033070 A1 * | 2/2005 | Cadwallader | C11C 3/003 554/176 |

* cited by examiner

CETYLATED FATTY ACIDS, SYSTEM FOR THE PREPARATION THEREOF AND USE THEREOF

CROSS-REFERENCE TO RELATED APPLICATIONS

This application is a § 371 national phase of International Application No. PCT/IB2016/054788, filed on Aug. 9, 2016, which claims the benefit of Italian Application No. 102015000044822, filed on Aug. 14, 2015, which applications are incorporated by reference herein.

The present invention relates to a process for preparing a mixture of cetylated fatty acids and a system for carrying out said process. Furthermore, the present invention relates to a composition comprising or, alternatively, consisting of said mixture of cetylated fatty acids. Finally, the present invention relates to said composition for use in the treatment and/or prevention of: (i) rheumatoid arthritis of inflammatory and non-inflammatory origin, in particular osteoarthritis; (ii) other inflammatory joint conditions; (iii) psoriasis, lupus, periodontal diseases or cardiovascular or heart diseases; (iv) all post-traumatic osteoarticular pathologies including sports injuries; (v) all degenerative joint pathologies (arthrosis, gonarthrosis, coxarthrosis, etc.) and (vi) inflammatory-traumatic tendon and muscular conditions. Furthermore, it is envisaged that the composition of the present invention be used in the treatment and/or prevention of the above-mentioned pathologies and disorders (i)-(vi) in association with a rehabilitative therapy. The composition comprising said mixture is formulated in a pharmaceutical form for oral use (novel food, supplement or medical device), i.e. in the form of a pill, pastille, capsule, tablet, granules, dispersible powder, syrup, solution, sprayable solution; for topical use (composition for a medical device), i.e. in the form of a cream, unguent, ointment, gel or spray to be used as such for application on the skin, or else for transdermal use in the form of a patch.

It is well known that an esterification reaction between a fatty acid and a long-chain alcohol (longer than C12) or high molecular weight alcohol (MW greater than 200) can be conducted in the presence of a chemical solvent, such as toluene, which behaves like an azeotropic solvent for the removal of the esterification water. An acid catalyst such as sulphuric acid is also used in the reaction and the process is conducted in a reactor equipped with a Marcusson apparatus. When such a process is used, the final ester product, which has a waxy consistency, appears black in colour due to the presence of sulphuric acid, which provokes a partial carbonisation of the final ester product. The black colour can be removed by washing with diluted alkalis, which neutralise the catalyst, and sodium chloride, which favours the separation of the phases. Using this type of process, it is necessary, moreover, to completely remove the solvent used from the final ester product. Complete removal of the solvent is not always easy to achieve, and in any event represents a cost and a major technological complication. As a result of said mandatory steps at the end of the esterification reaction, this known process is costly and requires rather complex technologies. Furthermore, the use of solvents during the esterification reaction does not always guarantee a complete and total removal thereof from the final product and there is always a risk of having a residual content of solvents in the final product that can exceed the limits imposed by the regulatory authorities for medical or cosmetic applications. That is the reason why use of a final product obtained by using solvents, even if it undergoes a large reduction in the amount of the same, can encounter regulatory obstacles if used for oral or topical application.

G. Bartoli et al. (*Adv. Synth. Catal.* 2005, 1, 33-38) describe a method for the esterification of carboxylic acids with alcohols in the presence of zinc perchlorate hexahydrate as the catalyst and magnesium sulphate as a dehydrating agent.

The presence of a solid dehydrating agent entails additional filtration and purification steps, which are particularly undesirable for large-scale reactions.

It is important, moreover, to highlight that the perchlorate ion is a strong oxidising agent which, even at relatively low temperatures, causes degradation of the alkyl compounds such as the reagents and reaction product to which the present invention relates. This is true in the specific case of structures containing unsaturated systems. Furthermore, the presence of perchlorates can also represent a hazard, since perchloric acid and the salts thereof may also provoke explosions in the reaction medium.

Another important factor is that perchloric acid, like sulphuric acid and p-toluenesulphonic acid, catalyses a parasite reaction resulting in the formation of estolides of the unsaturated fatty acids, i.e. of esters of long-chain acids formed from hydroxy acids by esterification of two acids having the same structure or different formulas, which are undesirable by-products, for example via formation of an epoxide on the double bond of an unsaturated fatty acid. There thus remains a need to be able to have a process (and an associated system) that is easy to carry out, economical and capable of preparing, with a high yield, an ester as a raw material to be used in a composition of a finished product for oral and topical use. It is desirable to be able to have a process (and an associated system) that does not require removal of a solvent at the end of the esterification reaction, but nonetheless enables removal both of the water produced during the esterification reaction to favour the progress of the reaction and the unreacted compounds at the end of the reaction itself. Furthermore, it is desirable to be able to have a process (and an associated system) that does not give rise to secondary reactions or reaction by-products, such as, for example, estolides.

However, simply applying a vacuum during an esterification reaction has the effect not only of removing the water produced from the reaction vessel, but also of removing the starting reagents (i.e. the fatty acid and the cetyl alcohol) that have not yet reacted. As a result, not only is the reaction yield lowered, but an occlusion can occur in the condenser located before the vacuum pump and after the reactor or reaction vessel, even in the initial phases of the reaction. Therefore, also from a plant engineering viewpoint, a need is felt to introduce changes/improvements to existing systems in order to overcome the limits and drawbacks present in them.

The Applicant, after lengthy and intense research activity, has surprisingly found that the above-mentioned disadvantages can be overcome thanks to the process (and associated system) as described below. Thanks to the process and associated system here described and claimed, the Applicant is able to prepare a mixture of cetylated fatty acids easily and cost-effectively, with a very high reaction speed and very high yields, without a solvent, and in a manner suitable for preparing a pharmaceutical composition or a composition for a medical device or a supplement for oral use in the form of a pill, pastille, capsule, tablet, granules, dispersible powder, syrup, solution, sprayable solution; or for topical use in the form of a cream, unguent, ointment, gel or spray to be used as such for application on the skin, or else for transdermal use in the form of a patch.

DESCRIPTION

Figure 1:
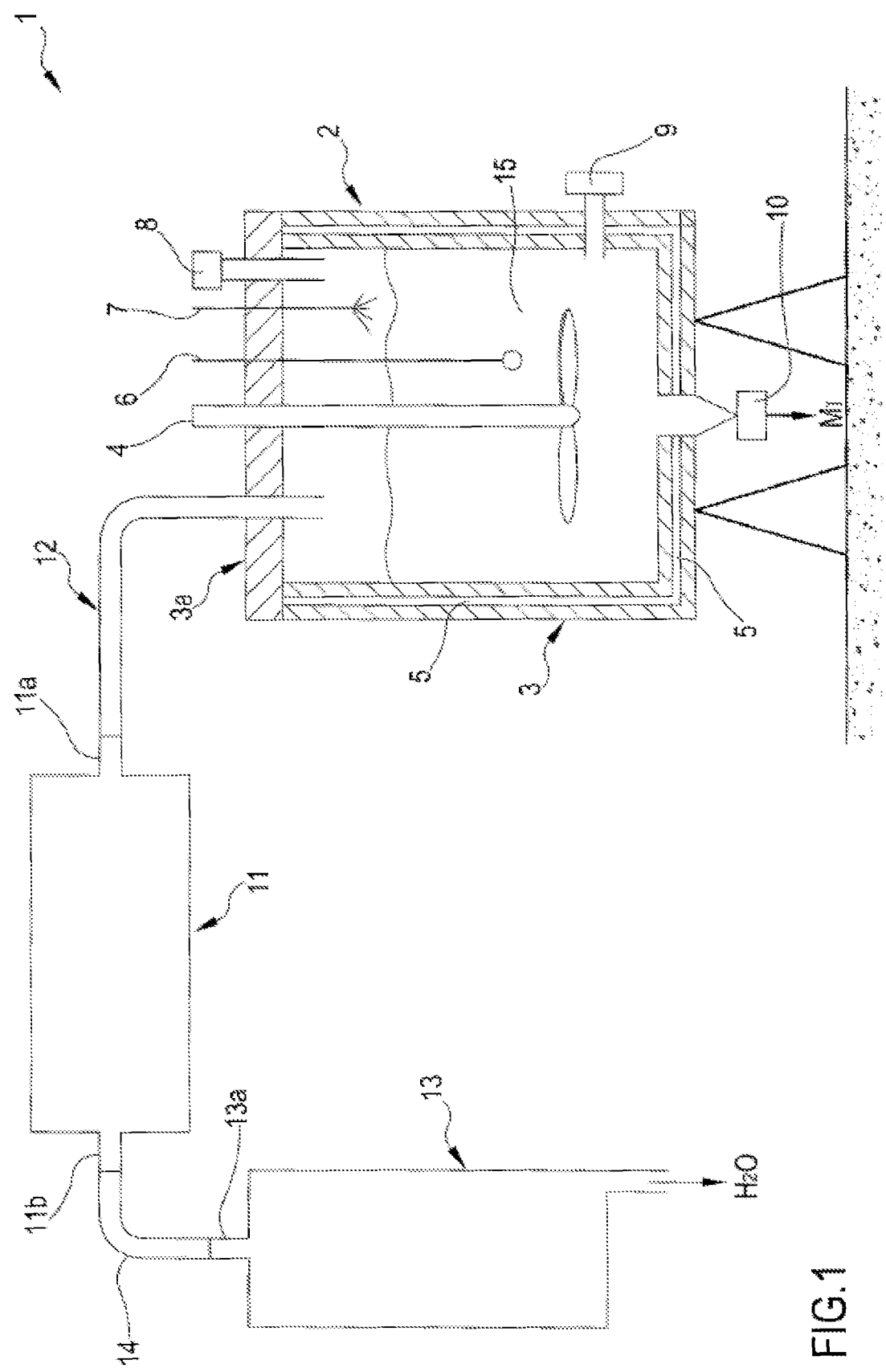
FIG. 1 schematically illustrates a first system and method (referred to as "method I" below).

The present invention relates to a process for preparing a mixture of cetylated fatty acids, as claimed in the appended claims.

The present invention relates to a system for preparing said mixture of cetylated fatty acids, in accordance with the process of the present invention, as claimed in the appended claims.

The present invention relates to a composition comprising said mixture of cetylated fatty acids, as claimed in the appended claims.

The present invention relates to a composition comprising said mixture of cetylated fatty acids for use in the treatment and/or prevention of: (i) rheumatoid arthritis of inflammatory and non-inflammatory origin, in particular osteoarthritis; (ii) other inflammatory joint conditions; (iii) psoriasis, lupus, periodontal diseases or cardiovascular or heart diseases; (iv) all post-traumatic osteoarticular pathologies including sports injuries; (v) all degenerative joint pathologies (arthrosis, gonarthrosis, coxarthrosis, etc.) and (vi) inflammatory-traumatic tendon and muscular conditions, as claimed in the appended claims.

The present invention relates to the composition for use in the treatment and/or prevention of the above-mentioned pathologies and disorders (i)-(vi) in association with a rehabilitative therapy.

Said mixture of cetylated fatty acids and said composition containing the same are capable of modulating and reducing inflammatory mechanisms rapidly and effectively, thus providing a very strong anti-inflammatory activity.

Preferred embodiments of the present invention are described below in detail without any intention of limiting the scope of the invention itself.

The process of the present invention comprises a step in which at least one fatty acid of plant or animal origin (reaction reagent) is placed in contact with a cetyl alcohol (reaction reagent) [1-hexadecanol, CAS 36653-82-4, EINECS 253-149-0] and a catalyst, in the absence of a solvent (such as, for example, in the absence of water or in the absence of any organic solvent or inorganic solvent). The two reaction reagents are placed in contact at an initial pressure of about 1 atmosphere (1 atm=1.01 bar). Throughout the whole course of the esterification reaction, the pressure can remain constant at about 1 atmosphere, or else it can be reduced, as better described below, by setting a vacuum program for the whole course of the reaction.

The fatty acids are of plant or animal origin and are selected from the group comprising or, alternatively, consisting of myristic acid, for example myristic acid of the type [tetradecanoic acid, CAS 544-63-8, EINECS 208-875-2], oleic acid, for example oleic acid of the type [CAS 112-80-1, EINECS 204-007-1] and mixtures thereof. The myristic acid can be a myristic acid with a purity comprised from 90% to 99%, preferably from 94% to 98%. The oleic acid can be an oleic acid with a purity comprised from 70% to 95%, preferably from 75% to 90%, even more preferably from 80% to 85%.

In a preferred embodiment, the starting mixture of fatty acids can comprise from 50% to 99% by weight of myristic acid, for example myristic acid of the type [tetradecanoic acid, CAS 544-63-8, EINECS 208-875-2] and from 1% to 50% by weight of oleic acid, for example oleic acid of the type [CAS 112-80-1, EINECS 204-007-1].

In another preferred embodiment, the starting mixture of fatty acids can comprise from 60% to 90% by weight of myristic acid, for example myristic acid of the type [tetradecanoic acid, CAS 544-63-8, EINECS 208-875-2] and from 40% to 10% by weight of oleic acid, for example oleic acid of the type [CAS 112-80-1, EINECS 204-007-1].

For example, the starting mixture of fatty acids comprises about 65% by weight of myristic acid, for example myristic acid of the type [tetradecanoic acid, CAS 544-63-8, EINECS 208-875-2] and about 35% by weight of oleic acid, for example oleic acid of the type [CAS 112-80-1, EINECS 204-007-1]. The catalyst is a metal catalyst and can preferably be zinc powder. In one embodiment, the catalyst used is zinc metal powder. The amount of catalyst added is comprised from 0.05% to 0.3% by weight relative to the total weight of the reaction reagents (i.e. fatty acid or mixture of fatty acids+cetyl alcohol). Preferably, the amount of catalyst added is comprised from 0.1% to 0.25% by weight; even more preferably, it is comprised from 0.15% to 0.20% by weight.

It has been found that the use of a metal powder catalyst such as, for example, zinc metal powder, is particularly advantageous because, besides ensuring excellent yields and a high purity of the reaction product, it can be easily removed from the final mixture by filtration. For example, the content of zinc in the final product obtained through the process of the invention is equal to or less than 20 ppm. This content is perfectly compatible with use of the reaction product for pharmaceutical or cosmetic purposes, also considering that zinc has a tolerability that is considerably higher than that of other metals, such as, for example, tin and titanium, which can be used as catalysts in esterification reactions in the form of salts, e.g. chlorides or oxides.

The reaction is conducted at a temperature comprised from 150 C.° to 200° C., preferably at a temperature comprised from 160° C. to 190° C., even more preferably at about 180° C. The reaction time is comprised from 1 hour to 10 hours, preferably from 1 hour to 8 hours, preferably from 4 hours to 7 hours. The person skilled in the art is aware of the fact that the reaction time depends on the reaction conditions used (temperature, pressure, type of catalyst and reagent concentrations).

The removal of the reaction water that is formed during the esterification reaction is a necessary step in order to reach an optimal conversion/reaction yield. The removal of water from the reaction environment can be achieved by vacuum distillation performed throughout the whole esterification reaction in the reactor, using a vacuum program that applies a reduction in the reaction pressure in a non-linear manner (see method II and apparatus II described below). In this case the vacuum program is applied to the whole system and the whole process. Alternatively, the removal of water from the reaction environment can be achieved at a constant pressure of about 1 atm by using a flow of inert gas introduced into the reaction environment during the esterification reaction. The flow of inert gas serves to convey/draw the reaction water formed from the reaction environment (see method I and apparatus I described below).

It has been found that the use of an inert gas, such as, for example nitrogen, argon or mixtures thereof, also has a protective effect against oxidation of the material, particularly with respect to unsaturated systems, such as that of myristoleic acid or other unsaturated fatty acids that may be present (e.g. palmitoleic, oleic, linoleic and linolenic acid).

Advantageously, it has been found that the final product of the process according to the present invention (indicated as MI in FIGS. 1-4) has a high purity, for example greater than 95%. In fact, using suitable analytical methods such as gas chromatography with a flame ionisation detector (GC-FID), no impurities such as oxidation by-products or estolides, which are generally obtained in substantial amounts under esterification conditions according to the prior art, were detected.

Typically, the reaction yield is greater than 95%, and the mixture at the end of the reaction contains no more than 3% of cetyl alcohol and no more than 1.4% of the starting fatty acid mixture (weight/total weight of the mixture MI). After filtration of the catalyst and, optionally, a deodorant treatment to yield MF (FIGS. 1-4), for example at 180° C. and at a residual pressure of 10 mbar, the content of cetyl alcohol is less than 1.5% and the content of the fatty acid mixture is less than 0.9%. A purity greater than 97.5% is obtained. The Applicant has surprisingly found that by applying a vacuum program, carefully selected according to the degree of progress of the reaction, it is possible to favour the progress of the reaction by removing only the water without inducing the distillation of the reagents, above all in the early phases of the reaction, for example within the first two/three hours (see method II, apparatus II).

In one embodiment, the reaction is conducted by applying a vacuum program (reducing the pressure inside the reactor and the whole system in a non-linear manner—see method II, apparatus II) in which the applied pressure is, for example, equal to 600 mbar and is reduced, in a non-linear manner, to 5 mbar, for example after 7 hours. Preferably, the initial reaction pressure is about 1 atm and then a reduction is applied in the pressure, which is, for example, equal to 600 mbar during the first hour and then falls, for example, to 500 mbar 2 hours after the start, 300 mbar 3 hours after the start, 200 mbar 5 hours after the start and 5 mbar 7 hours after the start (total reaction time of 7 hours). Other vacuum programs can also be used.

The Applicant has found it useful and advantageous to equip the reactor of the system of the present invention with a vertical condenser and a horizontal condenser, arranged in series and temperature controlled (see method II, apparatus II) or, alternatively, with a horizontal condenser only (see method I, apparatus I). The vertical condenser is maintained at a temperature comprised from 70° C. to 90° C., preferably at a temperature of about 80° C., whereas the horizontal condenser is, in both cases, maintained at a temperature comprised from 10° C. to 40° C., preferably at a temperature of about 25° C. The vertical condenser favours the evaporation of water and simultaneous condensation of the reagents, which are thus recycled in the reaction vessel. It has moreover proven to be particularly advantageous, in both cases, to pass a flow of inert gas through the reactor during the reaction. Preferably, said inert gas is a nitrogen gas.

In said first embodiment (method I, apparatus I), the inert gas is introduced into the reaction environment, preferably as a continuous flow, not into the reaction mass, but rather in the volume above (at the head of the reactor) said reaction mass contained in the reactor.

In said second embodiment (method II, apparatus II), the inert gas is introduced into the reaction environment, preferably as a continuous flow, into the reaction mass present in the reactor (added in mass) by means of a conduit inserted within the reaction mass.

The present invention relates to a system for carrying out the process for preparing a mixture of cetylated fatty acids comprising or, alternatively, consisting of cetyl myristate and/or cetyl oleate.

In a first embodiment schematised in FIG. 1 (method I), the system 1 comprises a reactor 2 represented by a container 3 provided with a mixing means 4, such as, for example, a mechanical stirrer, a heating means 5, such as, for example a jacket fashioned on the outer surface of the container 3, inside which a heated fluid is made to pass, a means 6 for controlling the temperature inside the container, a means 7 for blowing an inert gas inside the container, an inlet port 8 fashioned in the upper part of the container 3a so as to enable the introduction of the solids or reagents, an outlet port 9 fashioned in the lower side part of the container 3 so as to enable the collection of reaction samples, and a valve 10 enabling the discharge of the mixture at the end of the process.

The reactor 2, via the container 3, is connected to a horizontal condenser 11, having a first inlet end 11a and a second outlet end 11b, by means of a conduit 12. The main axis of the horizontal condenser 11 is positioned in a manner substantially parallel to the rest surface of the reactor 2. The conduit 12 is positioned between the upper part of the container 3a and said first inlet end of the horizontal condenser 11a. The horizontal condenser 11 is connected to a container 13 for collecting the reaction water by means of a conduit 14. The conduit 14 is positioned between said second outlet end 11b and the upper part of the container 13a.

In a first embodiment, the process (I), for preparing a mixture of cetylated fatty acids comprising or, alternatively, consisting of cetyl myristate and/or cetyl oleate is carried out using the system in FIG. 1.

The process comprises a step in which the oleic and/or myristic acid are placed in contact in order to react with the cetyl alcohol in the presence of a catalyst such as metal zinc, so as to yield a reaction mixture 15. For the purpose of carrying out this step, said fatty acids, the cetyl alcohol and, at a later time, when the mass of reactive substances is in a melted state, the catalyst (in the absence of solvents) are loaded into the reactor 2 by introducing them through the port 8.

The reaction mixture is brought to a reaction temperature equal to or less than 100° C. and a pressure of about 1 atm. For heating purposes, a heated fluid, such as, for example a heated oil or water vapour is introduced under pressure, at a temperature such as to obtain the desired reaction temperature in the jacket 5 of the container 3. During the step of heating the reaction mixture 15, which is inside the reactor 2, the stirring means 4 and temperature control means 6 are activated and an inert gas, for example nitrogen, is blown/introduced into the container 3 via the blowing means 7. The inert gas, nitrogen, is not blown/introduced into the reaction mixture 15, but is rather introduced into the container 3, in the volume present above the reaction mixture 15. Said fatty acids, cetyl alcohol and catalyst (advantageously in the absence of solvents, pressure equal to about 1 atm and temperature comprised from 150° C. to 200° C.)

give rise to an esterification reaction within the reaction mixture 15, with the production of cetylated esters and esterification water. The esterification reaction is carried out without the use of a vacuum, but rather at a pressure of about 1 atm. The esterification water present in the reaction mixture 15, under the reaction temperature and pressure conditions, is transformed into water vapour, which is eliminated from the container 3. The water vapour is eliminated from the container 3 thanks to the flow of nitrogen introduced/blown into the part of the volume above the reaction mixture 15 (volume above the reaction mixture). The water vapour and nitrogen arrive at the horizontal condenser 11 via the conduit 12. The inert gas output from the container 3 passes through the conduits 12 and 14, is recovered and re-introduced into the container 3 (by means of a system of pipes and valves not shown in FIG. 1) thanks to the blowing means 7.

The horizontal condenser 11 has the purpose of condensing the esterification water, eliminating it from the reaction mixture 15 so as to drive the esterification reaction toward the greatest possible yield. The esterification water condensed into a liquid state is collected in the container 13 by means of the conduit 14. In order to achieve condensation of the esterification water, the condenser 11 is maintained at a temperature of less than 100° C., for example at a temperature comprised from 10° C. to 40° C., preferably from 20° C. to 30° C., and a pressure of about 1 atm. At the end of the esterification reaction (carried out without the use of solvents, at a pressure of about 1 atm and without a vacuum) the mixture of cetylated fatty acids is cooled and discharged through the valve 10.

Figure 2:
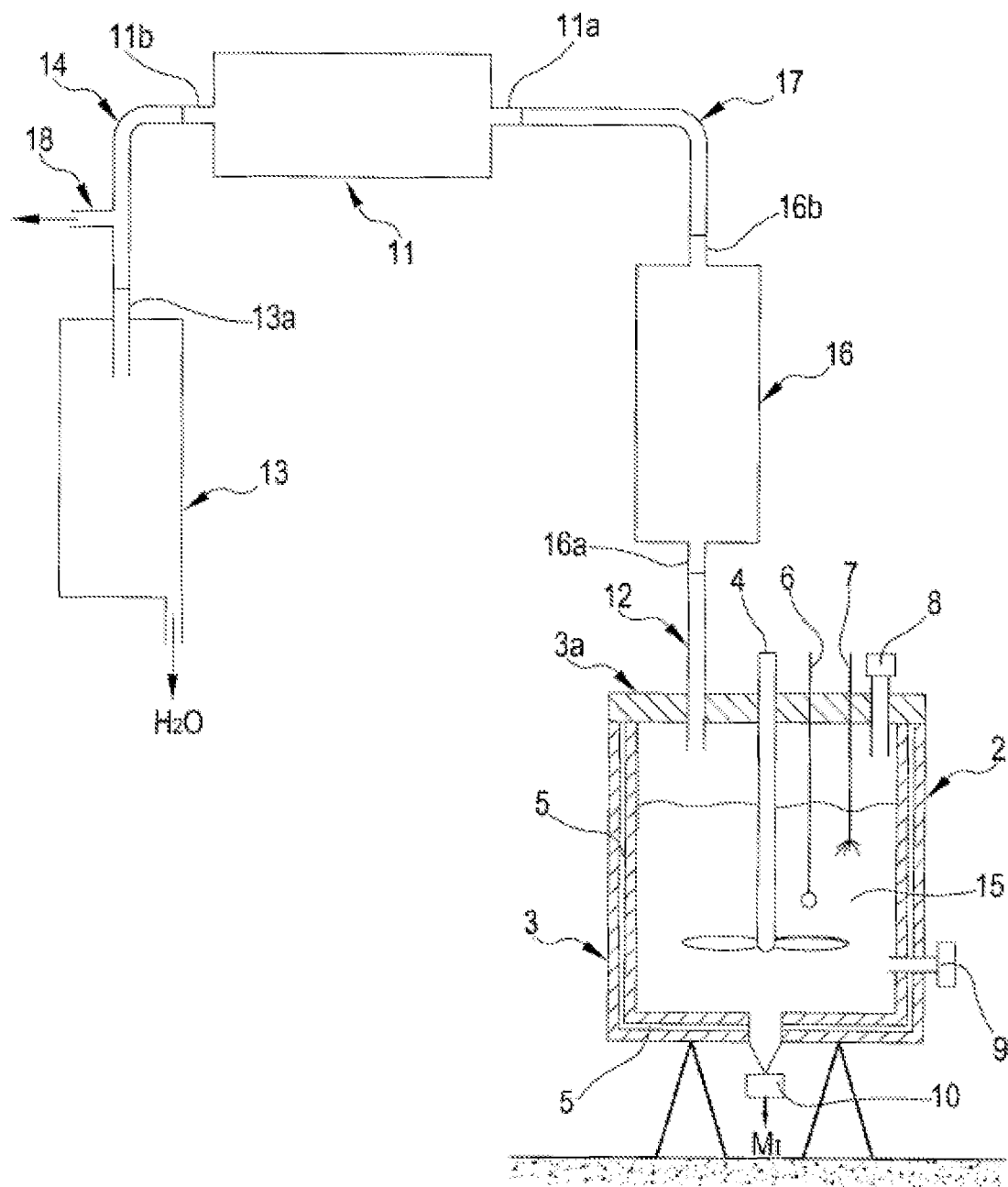
FIG. 2 schematically illustrates a second system and method (referred to as "method II" below).

In a second embodiment schematised in FIG. 2 (method II), the system 1 comprises a reactor 2 represented by a container 3 provided with a mixing means 4, for example a mechanical stirrer, a heating means 5, for example a jacket fashioned on the outer surface of the container 3, inside which a heated fluid is made to pass, a temperature control means 6 inside the container, a means 7 for blowing an inert gas into the reaction mixture 15 contained in the container 3, an inlet port 8 fashioned in the upper part of the container 3a in order to enable the introduction of solids or reagents, an outlet port 9 fashioned in the lower side part of the container 3 in order to enable the collection of reaction samples, and a valve 10 in order to enable the discharge of the mixture at the end the process.

The reactor 2, via the container 3, is connected to a vertical condenser 16 having a first inlet end 16a and a second outlet end 16b, by means of a conduit 12. The main axis of the vertical condenser 16 is positioned substantially perpendicularly to the resting surface of the reactor 2. The conduit 12 is positioned between the upper part of the container 3a and said first inlet end of the vertical condenser 16a. The vertical condenser 16 is connected to a horizontal condenser 11, having a first inlet end 11a and a second outlet end 11b, by means of a conduit 17. The main axis of the horizontal condenser 11 is positioned substantially parallel to the resting surface of the reactor 2. The conduit 17 is positioned between the end of the vertical condenser 16b and said first inlet end of the horizontal condenser 11a. The horizontal condenser 11 is connected to a container 13 for collecting the reaction water by means of a conduit 14. The conduit 14 is positioned between said second outlet end 11b and the upper part of the container 13a. The conduit 14 comprises an outlet 18 to a pump or device (not shown in FIG. 2) capable of creating a vacuum (pressure lower than 1 atm) or, rather, a vacuum program with a non-linear reduction in pressure. In a second embodiment, the process (II), for preparing a mixture of cetylated fatty acids comprising or, alternatively, consisting of cetyl myristate and/or cetyl oleate is carried out using the system in FIG. 2.

The process comprises a step in which the oleic and/or myristic acid are placed in contact in order to react with the cetyl alcohol in the presence of a catalyst such as metal zinc, so as to yield a reaction mixture 15. In order to carry out this step, said fatty acids, the cetyl alcohol and catalyst (in the absence of solvents) are loaded into the reactor 2 by introducing them through the port 8.

The reaction mixture is brought to a reaction temperature equal to or less than 100° C. and a pressure of about 1 atm or else a reaction temperature greater than 100° C., for example a temperature comprised from 150° C. to 200° C. For heating purposes, a heated fluid, such as, for example a heated oil or water vapour is introduced under pressure, at a temperature such as to obtain the desired reaction temperature in the jacket 5 of the container 3. During the step of heating the reaction mixture 15, which is inside the reactor 2, the stirring means 4 and the temperature control means 6 are activated and an inert gas, for example nitrogen, is blown/introduced into the container 3 via the blowing means 7. The inert gas, nitrogen, is blown/introduced into the reaction mixture 15. Said fatty acids, the cetyl alcohol and catalyst (advantageously in the absence of a solvent and at a temperature comprised from 150° C. to 200° C.) give rise to an esterification reaction within the reaction mixture 15, with the production of cetylated esters and esterification water. The esterification water present in the reaction mixture 15, under the temperature and pressure reaction conditions, is transformed into water vapour, which must be eliminated from the container 3 in order to increase the reaction yield. The water vapour is eliminated from the container 3 by means of a vacuum program with a non-linear pressure reduction that intervenes after the condenser 11. The water vapour and nitrogen arrive at the horizontal condenser 11 by means of the conduit 12. The inert gas output from the container 3 passes through the conduits 12, 17 and 14, is recovered and re-introduced into the container 3 (by means of a system of pipes and valves not shown in FIG. 2) thanks to the blowing means 7. The vertical condenser 16 (*hot*) has the purpose of favouring the evaporation of the reaction water and the simultaneous condensation of the reagents, which are thus recycled in the container 3 via the conduit 12. The water that evaporates reaches the condenser 11 via the conduit 17, whereas the condensation of the reagents and their re-introduction into the container 3 prevents the occlusion of the conduits and shutdown of the reactor 2.

The horizontal condenser 11 (cold) has the purpose of condensing the esterification water, eliminating it from the reaction mixture 15 in such a way as to drive the esterification reaction toward the highest yield possible. The esterification water condensed into the liquid state is collected in the container 13 via the conduit 14, which comprises a conduit 18 leading to a pump or device (not shown in FIG. 2) in order to carry out a vacuum program with a non-linear pressure reduction to facilitate the elimination of the esterification water. In order to bring about condensation of the esterification water, the condenser 11 is maintained at a temperature of less than 100° C., for example at a temperature comprised from 10° C. to 40° C., preferably from 20° C. to 25° C., and a pressure of about 1 atm.

At the end of the esterification reaction (carried out without the use of a solvent) the mixture of cetylated fatty acids is cooled and discharged from valve 10.

The myristic acid (tetradecanoic acid) used can be, for example, selected from those at a concentration of 99% CAS 544-63-8 (EINECS 208-875-2) having a % composition (GLC): lauric acid C12:0 less than or equal to 1; myristic acid C14:0 greater than or equal to 99%; palmitic acid C16:0 less than or equal to 1. The oleic acid used can be, for example, selected from among those having at least 78% oleic acid CAS 112-80-1 (EINECS 204-007-1) with a % composition (GLC) for example: [lauric acid+myristic acid] C12:0+C14:0 less than or equal to 0.5; oleic acid C18:1 greater than or equal to 78%; linoleic acid C18:2 less than or equal to 15 and others C18:3 less than or equal to 1.

The cetyl alcohol (1-hexadecanol) used can be, for example, selected from those identified as CAS 36653-82-4 (EINECS 253-149-0).

The mixture MI (FIG. 3) of cetylated fatty acids output from the valve 10 of the reactor 2 (FIGS. 1 and 2), obtained with the process described above (method I, apparatus I, or method II, apparatus II) comprises or, alternatively, consists of cetyl myristate and/or cetyl oleate, and a catalyst.

This "initial" mixture MI can be subjected to a subsequent refinement treatment to (i) reduce the amount of catalyst contained in it, (ii) deodorise the mixture and (iii) remove the reactive substances present in it which did not react. For this purpose, the mixture MI undergoes diatomaceous earth filtration in a filter press so as to yield a filtered mixture Mf in which the catalyst has been removed or greatly reduced in amount. The output filtered mixture Mf is introduced into a deodorising apparatus in order to be treated at a temperature comprised from 150° C. to 200° C., for example 180° C., at a residual pressure comprised from 5 mbar to 15 mbar, for example 10 mbar, in the presence of direct water vapour for a period of time comprised from 1 hour to 5 hours, preferably from 2 hours to 4 hours, for example 3 hours, so as to yield a "final" mixture MF. As regards the removal of the catalyst, the ICP-IES analysis performed on the "final" mixture MF revealed a residual zinc concentration of 19.6 mg/Kg in the reaction mixture, with a reduction of about 98% in the initial content of zinc metal powder introduced, which was equal to 1000 mg/Kg of reaction mixture.

Figure 3:
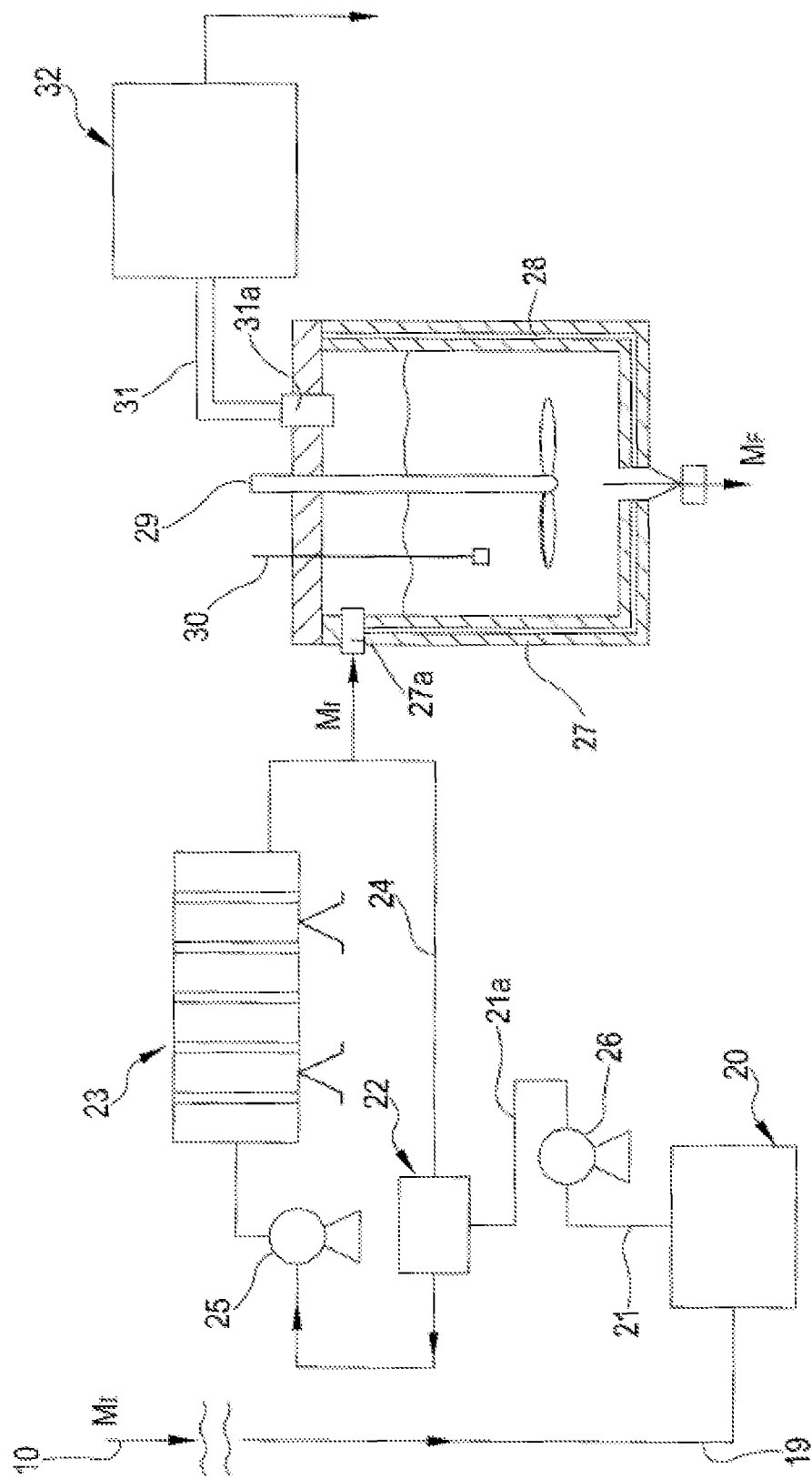
FIG. 3 schematically illustrates a method and system for refinement.

FIG. 3 shows the refinement treatment in which the mixture MI output from the valve 10 of the reactor 2 is introduced, by means of a pipe 19, into a mixer 20 where the diatomaceous earth is added. Via the conduits 21 and 21a, the mixture MI is introduced into the container 22 by means of the pump 26 positioned on the conduit 21, in order to be subjected to a series of steps inside the filter press 23 via the pipe 24 and the pump 25, in order to yield the filtered mixture Mf, in which the catalyst has been removed or greatly reduced in amount. The filtered mixture Mf output from the filter press 23 is introduced into the container 27 by means of the valve element 27a. The container 27 is provided with a heating means 28, a stirring means 29 and a water vapour blowing means 30. The deodorising and removal of the reagents from the mixture Mf is carried out, for example, at 180° C. and at a pressure of 10 mbar. A condenser 32 is placed on the outlet side of the container 27; it is connected, via the pipe 31, to a device for creating a vacuum (not shown in the figure). At the end of the refinement, one obtains the final refined mixture MF comprising or, alternatively, consisting of cetyl myristate and/or cetyl oleate and catalyst in minimum traces.

The final refined mixture MF, obtained as described above, has a vegetable oil added to it, such as a refined olive oil, in a ratio by weight 3:1 to yield the composition of the present invention; optionally said composition can further comprise pharmaceutical or food grade additives and excipients. The refined olive oil is added to the final refined mixture MF, cooled to about 100° C. before it solidifies.

In a preferred embodiment, said composition of the present invention comprises the mixture of cetylated fatty acids and a mixture of fatty acids of plant origin with a high content of oleic acid, from olive oil, palm oil and sunflower oil (HOSO) etc.; said mixture of cetylated fatty acids (obtained as described above) and said mixture of fatty acids of plant origin preferably being added in a ratio by weight of 5:1, 4:1, 3:1 or 2:1, advantageously in a ratio by weight of 3:1.

The composition of the present invention can further comprise a mixture of tocopherols and lecithin. The mixture of tocopherols can be present in an amount by weight comprised from 1% to 5%, preferably from 2% to 3%, relative to the total weight of the composition. The lecithin can be present in an amount by weight comprised from 1 to 10%, preferably in an amount from 1% to 5%, relative to the total weight of the composition.

In a particularly preferred embodiment, the composition of the present invention comprises 5% by weight of lecithin, 20% by weight of a refined olive oil, 74% by weight of cetylated fatty acids and 1% by weight of a mixture of tocophenols relative to the total weight of the composition.

The applicant has surprisingly found that the composition of the present invention is particularly useful in the treatment and prevention of (i) rheumatoid arthritis of inflammatory and non-inflammatory origin, in particular osteoarthritis; (ii) other inflammatory joint conditions; (iii) psoriasis, lupus, periodontal diseases or cardiovascular or heart diseases; (iv) all post-traumatic osteoarticular pathologies including sports injuries; (v) all degenerative joint pathologies (arthrosis, gonarthrosis, coxarthrosis, etc.) and (vi) inflammatory-traumatic tendon and muscular conditions. Furthermore, it is envisaged that the composition of the present invention will also be used in the treatment and/or prevention of the above-mentioned pathologies and disorders (i)-(vi) in association with a rehabilitative therapy.

The composition of the present invention does not have any side effects, such as kidney or heart dysfunctions, as opposed to known treatments.

Arthritis, or other inflammatory joint conditions include, but are not limited to, osteoarthritis, ankylosing spondylitis, cervical arthritis, fibromyalgia, osteonecrosis, Paget's disease, bursitis, psoriasis, gout, carpal tunnel syndrome, juvenile rheumatoid arthritis, lumbosacral arthritis, psoriatic arthritis and rheumatoid arthritis.

The composition comprising said mixture is formulated in a pharmaceutical form for oral use (novel food, supplement or medical device), i.e. in the form of a pill, pastille, capsule, tablet, granules, dispersible powder, syrup, solution, sprayable solution; for topical use (composition for a medical device), i.e. in the form of a cream, unguent, ointment, gel or spray to be used as such for application on the skin, or else for transdermal use in the form of a patch.

The term "patch" indicates a textile or synthetic medium that is capable of releasing cream in the skin area in which it is applied. When administered topically, the amount of composition administered is comprised from 1 to 15 mg/Kg of body weight per day. More preferably, the amount of the composition administered is comprised from 3 to 10 mg/Kg of body weight per day. More preferably, the amount of the composition administered is comprised from 5 to 8 mg/Kg of body weight per day.

The composition of the present invention can further contain other active ingredients and/or pharmaceutically acceptable additives, such as flavourings, stabilisers and antioxidants.

Method of Analysis

The reaction for synthesising the cetylated fatty acids, conducted with method II, apparatus II (FIG. 2), was controlled by means of GC-FID system (gas chromatography with a flame ionisation detector) consisting of:

Cool on-column injector;

Capillary column type SE-54 (DB-5, HP-5, etc.), length 15 metres, internal diameter 0.32 mm, film thickness 0.1 micron;

Flame ionisation detector (FID), set at a temperature of 370° C.;

Carrier gas: helium 1 ml/min (constant flow mode);

Oven temperature program: starting 50° C. (1 min)→180° C. (15° C./min)→230° C. (7° C./min)→360° C. (10° C./min) with final isothermy for 15 minutes.

A representative sample taken in an amount of about 5 mg was preliminarily treated with diazomethane in an ether solution for the derivation of the free —COOH groups, then diluted with heptane (8 ml) and injected.

Figure 4:
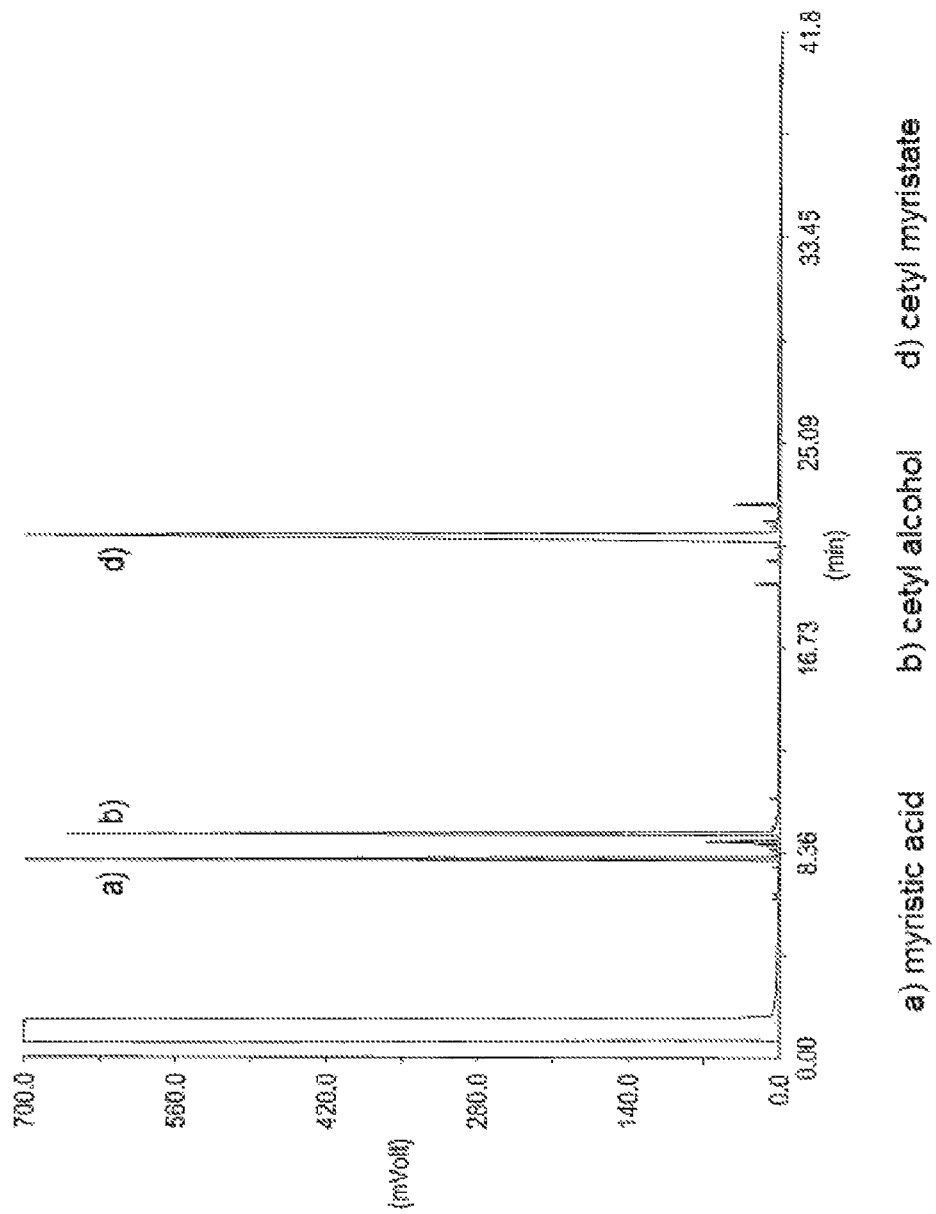
FIG. 4 shows a typical GC graph obtained from the analysis described in Example 1.
Figure 5:
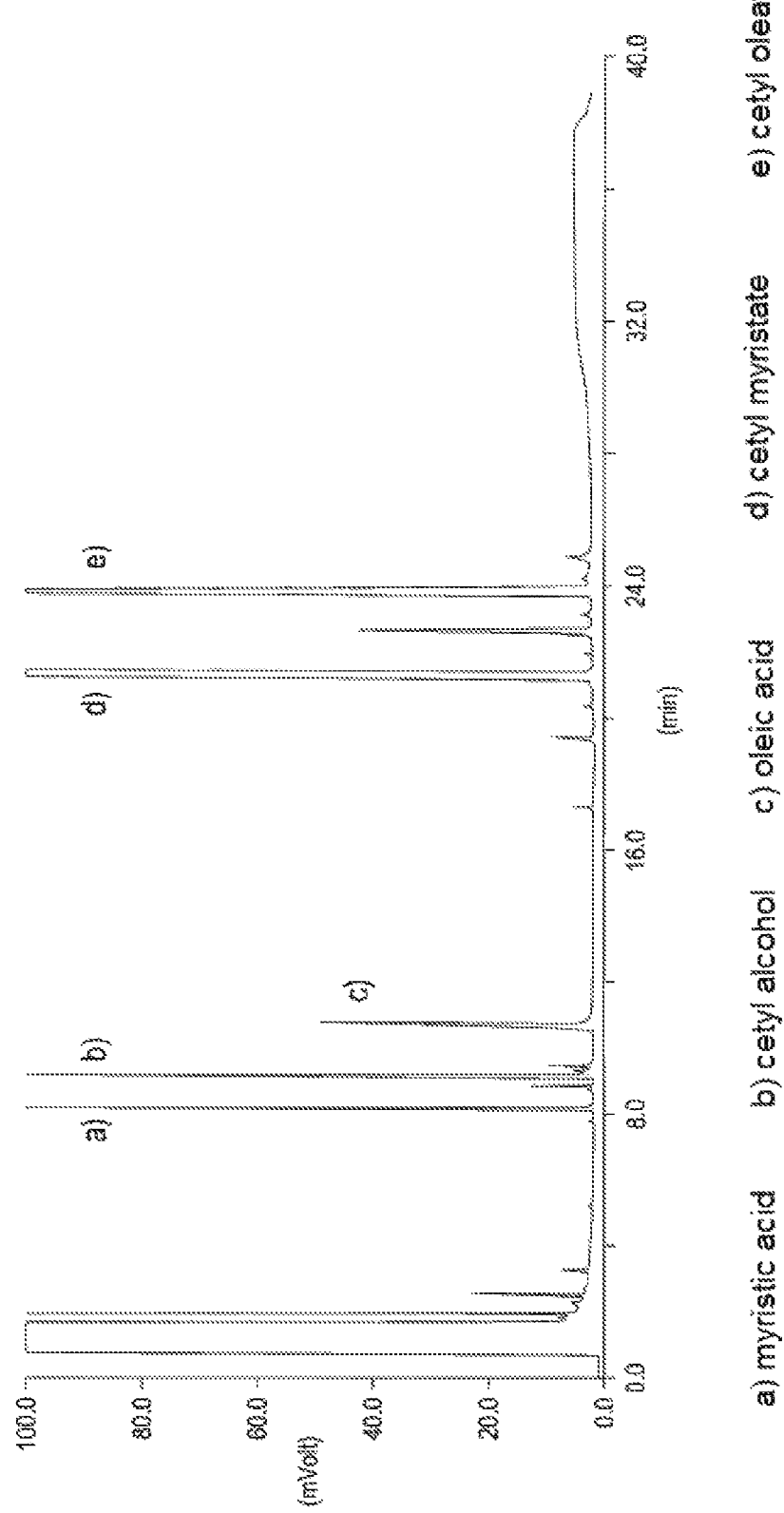
FIG. 5 shows a chromatogram obtained from the analysis described in Example 2 and 4.

FIG. 4 (Example of GC-FID analysis for the synthesis of cetyl myristate) shows a typical GC graph obtained in the case of synthesis of cetyl myristate as in Example 1. When oleic acid is used as a starting material together with myristic acid (Examples 2 and 4), the chromatogram obtained is the one in FIG. 5 (Example of GC-FID analysis for the synthesis of cetyl myristate/oleate).

The retention times (RT) in minutes are:

8.025 for myristic acid;
9.044 for cetyl alcohol;
10.550 for oleic acid+others C18;
21.167 for cetyl myristate;
22.416 for cetyl palmitate;
23.608 for cetyl oleate+cetyl others C18.

The presence of cetyl palmitate is justified by the composition of the mixture of oleic acid used. Examples of embodiments carried out without solvent in a reactor equipped with a vertical condenser heated to 80° C. and a horizontal condenser to 20° C. (method II and apparatus II):

EXAMPLE 1

Myristic acid (molecular weight 228), 50.0 g (0.219 moles). Cetyl alcohol (molecular weight 242), 53.0 g (0.219 moles). Catalyst: Zinc (Zn) metal powder, 0.1% (0.1 g). Temperature 180° C. At the end of the reaction the sample was filtered.

TABLE 1

| Reaction time, h | % acid | % alcohol | % wax | Residual pressure, mbar |
|---|---|---|---|---|
| 1 | 16.2 | 16.3 | 67.4 | 600 |
| 2 | 9.8 | 9.6 | 80.5 | 500 |
| 3 | 5.9 | 6.2 | 87.9 | 300 |
| 5 | 2.3 | 2.0 | 95.7 | 200 |
| 7 | 1.7 | 1.5 | 96.9 | 5 |

EXAMPLE 2

Myristic acid (molecular weight 228), 65.0 g (0.285 moles). Oleic acid 80% (molecular weight 274), 35.0 g (0.128 moles) [acidity 204.7 NS 200.5 mg KOH/g]. Total moles of acid: 0.413. Cetyl alcohol (molecular weight 242), 100.0 g (0.413 moles). Catalyst: Zn powder, 0.1% (0.2 g). Temperature 180° C. At the end of the reaction the sample was filtered. No occlusion of the condenser occurred in the initial phases of the reaction.

TABLE 2

| Reaction time, h | % acid | % alcohol | % wax | Residual pressure, mbar |
|---|---|---|---|---|
| 1 | 17.9 | 18.3 | 67.9 | 600 |
| 2 | 10.4 | 10.8 | 78.7 | 500 |
| 3 | 6.6 | 7.2 | 86.2 | 300 |
| 5 | 4.2 | 4.9 | 90.9 | 200 |
| 7 | 2.4 | 2.5 | 95.1 | 5 |

EXAMPLE 3

Cetyl alcohol (molecular weight 242), 100.0 g (0.413 moles). Oleic acid 80% (molecular weight 274), 112.0 g (0.409 moles). Catalyst: Zn powder, 0.1% (0.2 g). Temperature 180° C. At the end of the reaction the sample was filtered. No occlusion of the condenser occurred in the initial phases of the reaction.

TABLE 3

| Reaction time, h | % acid | % alcohol | % wax | Residual pressure, mbar |
|---|---|---|---|---|
| 1 | 19.1 | 19.3 | 61.6 | 600 |
| 2 | 10.6 | 12.0 | 77.4 | 500 |
| 3 | 6.7 | 8.2 | 85.1 | 300 |
| 5 | 3.5 | 5.3 | 91.2 | 200 |
| 7 | 1.4 | 3.1 | 95.5 | 5 |

EXAMPLE 4

Myristic acid (molecular weight 228), 160.0 g (0.701 moles). Oleic acid 80% (molecular weight 274), 88.0 g (0.321 moles) [acidity 204.7 NS 200.5 mg KOH/g]. Total moles of acid: 1.022. Cetyl alcohol (molecular weight 242), 250.0 g (1.033 moles). Catalyst: Zn powder, 0.1% (0.2 g). Temperature 180° C. Light flow of nitrogen in the reactor. At the end of the reaction the sample was filtered. No occlusion of the condenser occurred in the initial phases of the reaction.

TABLE 4

| Reaction time, h | % acid | % alcohol | % wax | Residual pressure, mbar |
|---|---|---|---|---|
| 1 | 15.6 | 12.6 | 71.8 | 600 |
| 2 | 10.0 | 6.7 | 83.3 | 500 |
| 3 | 6.8 | 3.7 | 89.5 | 300 |
| 5 | 4.7 | 1.6 | 93.6 | 200 |
| 7 | 3.5 | 0.8 | 95.7 | 5 |

Determination of the Melting Point of the Compositions Obtained According to NGD C27-1976

Given the very characteristics of the fatty substances, the melting point is well defined by the measurement of the slip and clear points. These temperatures correspond to those at which the fraction of a substance in contact with the walls of the capillary tube begins to melt (slip point) and then slip and run inside the capillary tube itself (clear point). In order to measure them, the substance in question is placed in a special U-shaped tube of well-established dimensions (for thermal aspiration of the melted sample at a temperature of about 10° C. above the melting point) and allowed to solidify for a time of at least 16 hours and then the water bath it is immersed in is heated very slowly. A mixture consisting of cetyl myristate (75% by weight) from Example 1 and refined olive oil (25% by weight) has: a slip point of 44.9° C. and a clear point of 47.1° C. A mixture consisting of cetyl myristate and cetyl oleate (75% by weight) from Example 2 and refined olive oil (25% by weight) has a slip point of 44.4° C. and a clear point of 45.1° C. A mixture consisting of cetyl myristate and cetyl oleate (75% by weight) from Example 4 and refined olive oil (25% by weight) has a slip point of 44.2° C. and a clear point of 45.2° C.

Experimental Design

In vitro study of effectiveness—in vitro assessment of the anti-inflammatory activity of a sample of a mixture of cetylated fatty acids obtained with method I of the present invention on a cell culture. The aim of the present study was to assess, in an in vitro system, the capacity of said sample to modulate the inflammatory mechanisms induced in cultures of human synovial cells (fibroblast-like synoviocytes) (ATCC-HTB-93). The study of the anti-inflammatory activity was conducted via an assay, using the ELISA method, of several markers of inflammation, specifically, three pro-inflammatory cytokines: TNFalpha, IL1alpha and IL6.

Preparation of the Samples and Method of Exposure

Before being tested for effectiveness, the sample was heated to 50° C. in a temperature-controlled bath kept under stirring to obtain a homogeneous solution. Then the sample was emulsified with corn oil (37° C.) and a culture medium was added to it as follows: 0.1 g emulsified with 100 µl of corn oil, brought to a volume of 1 ml with culture medium (37° C.). Then successive dilutions were made in the culture medium. The sample was subjected to a preliminary cytotoxicity test for the purpose of selecting the most suitable concentrations for the final test. To this end, concentrations ranging from 10.00% to 0.08% were tested (1:2 serial dilutions). Based on an assessment of the test results, 1.00% samples were selected for carrying out the study of anti-inflammatory activity. For the purpose of carrying out the test, the cultures of human synovial cells (fibroblast-like synoviocytes) (ATCC-HTB-93) were treated for 24 hours with LPS (lipopolysaccharide from *Escherichia coli*, 1 µg/ml), a known irritant agent of a bacterial nature, to induce acute inflammatory stress and simultaneously treated with the samples to be tested at the concentration of 1% selected on the basis of the preliminary cytotoxicity test. At the end of monitored experimental period, the levels of the cytokines of interest were measured in the culture media via an ELISA assay. The results were compared with negative control cultures (untreated, CTR−) and positive control cultures (treated only with LPS, CTR+). Summarising, the experimental protocol provided for an assay of three pro-inflammatory markers (TNFalpha, IL1alpha and IL6) in:
  untreated cell cultures (negative control, CTR−);
  cell cultures in which an event of acute inflammation was experimentally induced (positive control, CTR+);
  cell cultures in which an event of acute inflammation was experimentally induced and which were simultaneously treated with the test samples at 1.00%.

Assay of the Inflammation Markers (TNFalpha, IL1alpha and IL6)

The culture media of the controls and of the cells treated with the test samples were used to assay the pro-inflammatory cytokines TNFalpha, IL1alpha and IL6 using the ELISA method. For this purpose, use was made of commercially available kits which exploit the competitive binding of an antigen (in this case the cytokine of interest) with its primary antibody. The immune complex (antigen-antibody) is in turn recognised by a secondary antibody conjugated to a peroxidase. The addition of the peroxidase substrate produces a colorimetric reaction with an intensity proportional to the quantity of immune complexes present and thus to the quantity of bound cytokines. The quantitative determination relies on a calibration curve constructed with known standard cytokine concentrations on an increasing scale.

Results and Graphs

The tables that follow show the results obtained in the present study. The results are reported as the quantity of cytokines released in the culture media during the experimental period (mean value±SD) and as a mean % variation compared to the controls.

Anti-Inflammatory Activity—Assay of TNFalpha

TABLE 5

Assay of the TNFalpha in the cell cultures CTR−, CTR+ and treated with a sample of a mixture of cetylated fatty acids obtained with the method I (sample R8P). The results are expressed as mean content ± SD (expressed in ng/l) and as mean % variation compared to the controls. Table 5.

|  | TNFalpha ng/l | % Variation vs CTR− | % Variation vs CTR+ |
|---|---|---|---|
| CTR− | 145.7 ± 6.4 | — | — |
| CTR+ | 185.7 ± 12.3 | +27.5% | — |
| R8P 1.00% | 156.7 ± 6.4 | +7.5% | −15.6% |

Anti-Inflammatory Activity—Assay of IL1alpha

TABLE 6

Assay of the IL1alpha in the cell cultures CTR−, CTR+ and treated with the sample R8P. The results are expressed as mean content ± SD (expressed in ng/l) and as mean % variation compared to the controls. Table 6.

|  | IL1alpha ng/l | % Variation vs CTR− | % Variation vs CTR+ |
|---|---|---|---|
| CTR− | 115.6 ± 8.6 | — | — |
| CTR+ | 144.1 ± 5.9 | +24.7% | — |
| R8P 1.00% | 110.1 ± 8.3 | −4.7% | −23.6% |

Anti-Inflammatory Activity—Assay of IL6

TABLE 7

Assay of the IL6 in the cell cultures CTR−, CTR+ and treated with the sample R8P. The results are expressed as mean content ± SD (expressed in ng/l) and as mean % variation compared to the controls. Table 7.

|  | IL6 ng/l | % Variation vs CTR− | % Variation vs CTR+ |
|---|---|---|---|
| CTR− | 89.5 ± 9.1 | — | — |
| CTR+ | 105.6 ± 5.9 | +18.1% | — |
| R8P 1.00% | 73.7 ± 4.5 | −17.6% | −30.2% |

Embodiments of the present invention are indicated below with FRn:

FR1. A process for preparing a mixture of cetylated fatty acids (MI) comprising the steps of:
  placing in contact, in a container (3) of a reactor (2), at least one fatty acid selected from the group comprising or, alternatively, consisting of myristic acid, oleic acid or mixtures thereof, with a cetyl alcohol and a metal catalyst, in the absence of a solvent, so as to yield a reaction mixture (15);

heating said reaction mixture (15) to a reaction temperature comprised from 150° C. to 200° C. and a reaction pressure of about 1 atmosphere, so as to give rise to an esterification reaction with the initial formation of esters of cetylated fatty acids and esterification water;

allowing said reaction mixture (15) to react for a reaction time comprised from 1 hour to 8 hours until completion of said esterification reaction so as to obtain the complete formation of a mixture of cetylated fatty acids (MI) and the complete removal of said esterification water, the latter being achieved by introducing a flow of inert gas into the container (3) of said reactor (2) for the whole reaction time.

FR2. The process according to FR1, wherein said complete removal of esterification water is achieved by maintaining the reaction pressure constant at about 1 atm and introducing said flow of inert gas via a blowing means (7), into the portion of volume above the reaction mixture (15), thus allowing the esterification water to be drawn out of the container (3).

FR3. The process according to FR2, wherein the esterification water drawn out of the container (3) during the esterification reaction at a constant reaction pressure is condensed in a horizontal condenser (11) and collected in a container (13); preferably, said condenser (11) is maintained at a temperature comprised from 10° C. to 40° C. and is connected to said container (3), in the upper portion (3a) thereof, via the conduit (12).

FR4. The process according to FR1, wherein said complete removal of esterification water is achieved by using a vacuum program that applies a reduction in the reaction pressure in a non-linear manner and introducing said flow of inert gas, via the blowing means (7), into the reaction mixture (15), thus allowing the esterification water to be drawn out of the container (3).

FR5. The process according to FR4, wherein the vacuum program preferably applies a reduction in the reaction pressure to 600 mbar after the first hour of reaction in a non-linear manner, preferably arriving at 5 mbar after a reaction time of seven hours.

FR6. The process according to FR5, wherein the esterification water, drawn out of the container (3) during the esterification reaction with the vacuum program, is condensed in a horizontal condenser (11) and collected in a container (13) after having passed through a vertical condenser (16).

FR7. The process according to FR6, wherein said condenser (11) is maintained at a temperature preferably comprised from 10° C. to 40° C. and is connected to said container (3) via the vertical condenser (16), which is maintained at a temperature preferably comprised from 70° C. to 90° C.

FR8. The process according to any one of embodiments FR1-7, wherein said mixture of cetylated fatty acids (MI) is subjected to a subsequent refinement treatment, which comprises diatomaceous earth filtration in a filter press (23), so as to yield a filtered mixture Mf in which the metal catalyst present therein is removed or greatly reduced in amount.

FR9. The process according to FR8, wherein the filtered mixture Mf is treated in a reactor (27), at a temperature comprised from 150° C. to 200° C. and a pressure comprised from 5 mbar to 15 mbar in the presence of water vapour for a period of time comprised from 1 hour to 5 hours, so as to yield a final refined mixture (MF) based on cetylated fatty acids.

FR10. A composition comprising a final refined mixture (MF) based on cetylated fatty acids obtained according to FR9, and a vegetable oil in a 3:1 ratio by weight; said composition being for use in the treatment and prevention of (i) rheumatoid arthritis of inflammatory and non-inflammatory origin, in particular osteoarthritis; (ii) other inflammatory joint conditions; (iii) psoriasis, lupus, periodontal diseases or cardiovascular or heart diseases; (iv) all post-traumatic osteoarticular pathologies including sports injuries; (v) all degenerative joint pathologies (arthrosis, gonarthrosis, coxarthrosis, etc.) and (vi) inflammatory-traumatic tendon and muscular conditions.

The invention claimed is:

1. A process for preparing a mixture of cetylated fatty acids (MI) comprising the steps of:
    placing in contact, in a container (3) of a reactor (2), at least one fatty acid selected from the group comprising or, alternatively, consisting of myristic acid, oleic acid or mixtures thereof, with a cetyl alcohol and a metal catalyst, in the absence of a solvent, so as to yield a reaction mixture (15);
    heating said reaction mixture (15) to a reaction temperature comprised from 150° C. to 200° C. and a reaction pressure of about 1 atmosphere, so as to give rise to an esterification reaction with the initial formation of esters of cetylated fatty acids and esterification water;
    allowing said reaction mixture (15) to react for a reaction time comprised from 1 hour to 8 hours until completion of said esterification reaction so as to obtain the complete formation of a mixture of cetylated fatty acids (MI) and the complete removal of said esterification water, the latter being achieved by introducing a flow of inert gas into the container (3) of said reactor (2) for the whole reaction time.

2. The process according to claim 1, wherein said complete removal of esterification water is achieved by maintaining the reaction pressure constant at about 1 atm and introducing said flow of inert gas, via a blowing means (7), into the portion of volume above the reaction mixture (15), thus allowing the esterification water to be drawn out of the container (3).

3. The process according to claim 2, wherein the esterification water drawn out of the container (3) during the esterification reaction at a constant reaction pressure is condensed in a horizontal condenser (11) and collected in a container (13).

4. The process according to claim 1, wherein said complete removal of esterification water is achieved by using a vacuum program that applies a reduction in the reaction pressure in a non-linear manner and introducing said flow of inert gas, via the blowing means (7), into the reaction mixture (15), thus allowing the esterification water to be drawn out of the container (3).

5. The process according to claim 4, wherein the vacuum program applies a reduction in the reaction pressure to 600 mbar after the first hour of reaction in a non-linear manner.

6. The process according to claim 5, wherein the esterification water, drawn out of the container (3) during the esterification reaction with the vacuum program, is condensed in a horizontal condenser (11) and collected in a container (13) after having passed through a vertical condenser (16).

7. The process according to claim 6, wherein said condenser (11) is maintained at a temperature comprised from 10° C. to 40° C. and is connected to said container (3) via the vertical condenser (16).

8. The process according to claim 1, wherein said mixture of cetylated fatty acids (MI) is subjected to a subsequent refinement treatment, which comprises diatomaceous earth filtration in a filter press (23), so as to yield a filtered mixture Mf in which the metal catalyst present therein is removed or greatly reduced in amount.

9. The process according to claim 8, wherein the filtered mixture Mf is treated in a reactor (27), at a temperature comprised from 150° C. to 200° C. and a pressure comprised from 5 mbar to 15 mbar in the presence of water vapour for a period of time comprised from 1 hour to 5 hours, so as to yield a final refined mixture (MF) based on cetylated fatty acids.

* * * * *